US012751613B2

(12) United States Patent
Hendargo et al.

(10) Patent No.: US 12,751,613 B2
(45) Date of Patent: Oct. 6, 2026

(54) PROCESSING SYSTEM FOR OCT IMAGING, OCT IMAGING SYSTEM AND METHOD FOR OCT IMAGING

(71) Applicant: Leica Microsystems NC, Inc., Durham, NC (US)

(72) Inventors: Hansford Hendargo, Durham, NC (US); Eric Lynch, Apex, NC (US)

(73) Assignee: LEICA MICROSYSTEMS NC, INC., Durham, NC (US)

( * ) Notice: Subject to any disclaimer, the term of this patent is extended or adjusted under 35 U.S.C. 154(b) by 348 days.

(21) Appl. No.: 18/253,603

(22) PCT Filed: Nov. 18, 2021

(86) PCT No.: PCT/EP2021/082086
§ 371 (c)(1),
(2) Date: May 19, 2023

(87) PCT Pub. No.: WO2022/106510
PCT Pub. Date: May 27, 2022

(65) Prior Publication Data

US 2023/0414095 A1 Dec. 28, 2023

Related U.S. Application Data

(60) Provisional application No. 63/115,632, filed on Nov. 19, 2020.

(51) Int. Cl.
*A61B 3/10* (2006.01)

(52) U.S. Cl.
CPC .......... *A61B 3/102* (2013.01); *A61B 2505/05* (2013.01); *A61B 2576/02* (2013.01)

(58) Field of Classification Search
None
See application file for complete search history.

(56) References Cited

U.S. PATENT DOCUMENTS 8,018,598 B2 9/2011 Cense et al.
2007/0258094 A1 11/2007 Izatt et al.
(Continued)

OTHER PUBLICATIONS

Maciej Wojtkowski et al.: "Ultrahigh-resolution, high-speed, Fourier domain optical coherence tomography and methods for dispersion compensation", Optics Express, vol. 12, No. 11, May 31, 2004, pp. 2404-2422.

*Primary Examiner* — Christopher Koharski
*Assistant Examiner* — Farouk A Bruce
(74) *Attorney, Agent, or Firm* — LEYDIG, VOIT & MAYER, LTD.

(57) ABSTRACT

The invention relates to a processing system for use with optical coherence tomography imaging means for imaging a subject, the processing system being configured to repeatedly perform an image processing process (300), comprising the following steps: receiving (312) a scan data set from the subject (190) being acquired by means of optical coherence tomography, performing (314) data processing on the scan data set, including applying (316) dispersion correction based on a current set (370) of dispersion coefficients, and providing (318) a dispersion corrected image data set of the subject for an image of the subject to be displayed; and the processing system further being configured to repeatedly perform a dispersion coefficient adapting process (340), at least in part, in parallel to the image processing process (300), comprising the following steps: receiving (342) a scan data set from the subject being acquired by means of optical coherence tomography, adapting (344) dispersion coefficients by means of an optimization process (346) performed on the scan data set, and providing (348) a set (372) of adapted dispersion coefficients to be used to update the current set (370) of dispersion coefficients; and the processing system further being configured to update (350) the current set (370) of dispersion coefficients based on the (Continued)

set (372) of adapted dispersion coefficients, to an optical coherence tomography imaging system and a corresponding method.

15 Claims, 3 Drawing Sheets

(56) References Cited

U.S. PATENT DOCUMENTS

| | | | | |
|---|---|---|---|---|
| 2008/0181477 | A1 | 7/2008 | Izatt et al. | |
| 2009/0196477 | A1* | 8/2009 | Cense | G01B 9/02083 382/131 |
| 2011/0009752 | A1* | 1/2011 | Chen | A61B 5/0066 600/478 |
| 2013/0044330 | A1* | 2/2013 | Kang | G01B 9/02089 356/479 |
| 2013/0169971 | A1 | 7/2013 | Brown et al. | |

* cited by examiner

PROCESSING SYSTEM FOR OCT IMAGING, OCT IMAGING SYSTEM AND METHOD FOR OCT IMAGING

TECHNICAL FIELD

The present invention essentially relates to a processing system for use with optical coherence tomography (OCT) imaging means for imaging a subject, to an OCT imaging system including such processing system, and to a method for imaging a subject, using OCT.

BACKGROUND

Optical coherence tomography (in the following also called OCT, its typical abbreviation) is an imaging technique that uses low-coherence light to capture two- and three-dimensional images from within optical scattering media (e.g., biological tissue) with high resolution. It is, inter alia, used for medical imaging. Optical coherence tomography is based on low-coherence interferometry, typically employing near-infrared light. The use of relatively long wavelength light allows it to penetrate into the scattering medium. A medical field of particular interest for OCT is ophthalmology, a branch of medicine related to (in particular human) eyes and its disorders and related surgeries.

SUMMARY

According to the invention, a processing system, an OCT imaging system and a method for imaging a subject with the features of the independent claims are proposed. Advantageous further developments form the subject matter of the dependent claims and of the subsequent description.

The present invention relates to a processing system for use with optical coherence tomography (OCT) imaging means for imaging a subject, in particular, for real-time imaging of the subject. This subject, preferably, includes or is an eye. The type of OCT to be used is, preferably, spectral domain OCT (also known as Fourier domain OCT). The processing system can be comprised in a control unit that is configured to control the OCT imaging means. However, also only part of the processing system can be comprised in such control unit (thus, the control unit may be part of the processing system) as will be described later. While spectral or Fourier domain OCT can be based on a broad band light source and a spectrometer system (e.g., with a diffraction grating or other dispersive detector), also swept-source OCT (SS-OCT) can be used, in which a frequency of the light is varied over time (i.e., a spectrally scanning system).

In OCT, areas of the sample (subject) or tissue that reflect back a lot of light will create greater interference than areas that do not. Any light that is outside the short coherence length will not interfere. This reflectivity profile is called an A-scan and contains information about the spatial dimensions and location of structures within the sample or tissue. A cross-sectional tomograph, called B-scan, may be achieved by laterally combining a series of these axial depth scans (A-scan). A B-scan can then be used to create a two-dimensional OCT image to be viewed.

The processing system receives a scan data set from the subject being acquired by means of optical coherence tomography. The scan data set can include the intensity data for one or several depth-resolved reflectivity profiles of the sample, so-called A-scans. These raw data have to be processed in order to create an image to be viewed by, e.g., an operator of the OCT system on display means. Typically, OCT data processing requires resampling and taking the Fourier transforms of this real-valued spectral interferograms (the spectra included in the scan data set) to generate the depth-resolved reflectivity profiles of the sample, the A-scans.

In particular, Fourier domain optical coherence tomography (FD-OCT) uses the principles of low-coherence interferometry to generate two- or three-dimensional images of a subject (sample). OCT systems often have a mismatch in the optics used in the sample and reference arms due to the optical specification and requirements of the system. The mismatch may also be caused by the sample under interrogation itself. These differences cause an effect known as dispersion where the speed of different wavelengths depends upon the index of refraction of the medium. Thus, light may travel at variable speeds through each arm, which results in a temporal spreading of the coherent wave packets that interfere at the detector. This leads to a wavelength-dependent phase shift in the interferogram (spectrum) and causes blurring along the axial dimension in the final OCT image.

Thus, the data processing includes applying dispersion correction based on a set of dispersion coefficients (such set typically comprises several coefficients; however, such set could also comprise only a single coefficient, depending the circumstances). A dispersion corrected image data set of the subject for an image of the subject to be displayed is then provided. Such image processing process (including receiving the scan data set, performing the data processing and providing the dispersion corrected image data set) typically is repeatedly performed and, thus, allows real-time imaging of the subject.

Dispersive effects may be compensated by using a numerical correction which involves applying second and/or third order phase terms to the acquired interferometric spectrum. This requires the determination of the correction coefficients for each phase order, typically using an iterative optimization process that adjusts the coefficients to either maximize or minimize an image quality metric. Such techniques are described, for example, in "M. Wojtkowski, V. J. Srinivasan, T. H. Ko, J. G. Fujimoto, A. Kowalczyk, J. S. Duker, Ultrahigh-resolution, high-speed, Fourier domain optical coherence tomography and methods for dispersion compensation, Optics Express, 12(11), 2004.", in U.S. Pat. No. 8,018,598 B2, U.S. Pat. No. 8,401,257 B2 and U.S. Pat. No. 7,719,692 B2. This process is usually done once at the beginning of an acquisition or is computed for a given imaging configuration in a pre-acquisition calibration.

However, it has turned out that this method may result in sub-optimal dispersion correction, in particular, for situations where the optical medium of the sample (subject) changes during acquisition, such as during surgical procedures that involve gas and fluid exchanges.

Within the present invention, a new technique in order to better correct or compensate such dispersion effects is proposed. This includes a coefficient adapting process repeatedly performed on the processing system. In each cycle of that coefficient adapting process, a scan data set from the subject, being acquired by means of optical coherence tomography, is received at the processing system, dispersion coefficients are adapted by means of an optimization process performed on the scan data set, and then a set of adapted dispersion is provided that is to be used to update the current set of dispersion coefficients used in the image processing process mentioned before.

The repeatedly performed dispersion coefficient adapting process is, at least in part, performed in parallel to the repeatedly performed image processing process. Preferably, both processes are performed fully in parallel, i.e., simultaneously. This allows performing the image processing as usual; however, the dispersion coefficients used therein can be updated whenever an updated version is available from the simultaneously performed adaption process.

To sum up, this allows updating the dispersion correction coefficients dynamically, e.g., in response to changes in the optical medium of a given sample (subject). The method uses a separate computing or adapting process to determine the optimal (or at least better or adapted) coefficients while simultaneously performing standard processing of the OCT image to allow continual, real-time display. The coefficients are, preferably, continually updated to provide the best correction for dispersion in a given sample without needing to separately calibrate and stop the acquisition.

Logic can be used to determine whether the coefficients are updated continuously or only once certain criteria have been met, such as if the magnitude of the change in the coefficients exceeds a certain threshold. Additional checks can also be used to ensure that the OCT image of interest is corrected and not the conjugate image that results from the Fourier transform during processing.

In order to perform the two processes simultaneously, the processing system preferably comprises to processing units configure to be run in parallel and, preferably, also independently from each other, and each configured to perform one of the two processes, the image processing process and the dispersion coefficient adaption process. Each of the processing units can be either a CPU or a GPU. Thus, the processing system can comprise two CPUs, two GPUs or a CPU and a GPU. Note that also several CPUs or GPUs can be combined to form a processing unit in order to provide sufficient computing power.

As mentioned before, these two processes can be performed on either the same computer system (or control unit) used to run the software to control the OCT means or OCT system or on a separate computer system external to the OCT system. In the first case, the processing system is comprised in the control unit, in the second case, only the processing unit for performing the image processing system is comprised in the control unit, the other processing unit is provided separately and remote. This other processing unit for performing the dispersion coefficient adaption process can be a separate computer or PC in the same room as the OCT system; it can also be formed, however, by a server or cloud computing system connected via internet or the like.

A further advantage of the proposed technique is that the two processes do not need to be synchronized. This means that while in each cycle of an image processing process a new (and the next acquired) scan data set is used, in each cycle of an dispersion coefficient adaption process only the latest available scan data set is used. A simple example is that the duration of a dispersion coefficient adaption process performed on a scan data set is twice as long as the duration of an image processing process. Thus, two cycles of image processing are performed until the set of dispersion coefficients are updated. In other words, two cycles of the imaging process are performed based on the same set of dispersion coefficients (note that logic may nevertheless decide not to update the dispersion coefficients if, e.g., there was no major change).

The dispersion optimization may be performed on data from an entire OCT scan (which then corresponds to a scan data set) or a subset of such a scan (or scan data set). Further, the optimization process is, preferably, performed on an image based on the scan data set and uses an image quality metric. Such metric can be based on at least one of the following: a maximum image intensity, a sharpness of the image, a brightness of the image, and an overall signal-to-noise ration of the image. In other words, the optimization process may use an image quality metric to assess the effects of changing the coefficients and may include looking at the maximum image intensity, the sharpness of the image, the overall signal-to-noise ratio of the image, or other numerical method of quantifying the quality of the image.

The optimal coefficients can be determined from either the second order numerical correction or (also in addition) include higher orders (third order and up). Corrections may also be applied by computing different resampling parameters in addition to or without separate dispersion coefficients. Logic for determining the validity of computed dispersion coefficients may include looking for sign changes in the coefficients or analyzing image features such as gradients, histograms, or sample specific features that may indicate the presence of the conjugate image.

The invention also relates to an optical coherence tomography (OCT) imaging system for (in particular, real-time) imaging a subject, e.g. an eye, comprising the processing system according to the invention and as described above, and optical coherence tomography imaging means in order to perform the OCT scan (for a more detailed description of such OCT imaging means it is referred to the drawings and the corresponding description). Preferably, the OCT imaging system is configured to display an image of the subject on display means. Such display means can be part of the OCT imaging system.

Such OCT imaging system typically also comprises a control unit configured to control the optical coherence tomography imaging means. As mentioned before, the control unit can comprise the processing system and, in particular, both processing units mentioned above. However, the control unit may also comprise only the processing unit configure to perform the image processing process, while the other processing unit is provide separately.

The invention also relates to a method for imaging a subject like an eye, using optical coherence tomography (OCT), preferably, spectral domain OCT. The method comprises repeatedly performing the following steps of an image processing process: acquiring a scan data set from the subject by means of optical coherence tomography, performing data processing on the scan data set, including applying dispersion correction on the scan data set based on a current set of dispersion coefficients, and providing a dispersion corrected image data set of the subject for an image of the subject and, preferably, displaying the image of the subject. The method further comprises repeatedly performing a dispersion coefficient adapting process, at least in part, in parallel to the image processing process, comprising the following steps: receiving a scan data set from the subject being acquired by means of optical coherence tomography, adapting dispersion coefficients by means of an optimization process performed on the scan data set, and providing a set of adapted dispersion coefficients. The method also comprises updating the current set of dispersion coefficients based on the set of adapted dispersion coefficients. Both processes, image processing process and dispersion coefficient adapting process, are preferably performed on different processing units. The step of updating the coefficients typically is a step link both processes and processing units.

With respect to further preferred details and advantages of the OCT imaging system and the method, it is also referred to the remarks for the processing system above, which apply here correspondingly.

The invention also relates to a computer program with a program code for performing a method according to the invention when the computer program is run on a processor, processing system or control unit or system, in particular, like described before.

Further advantages and embodiments of the invention will become apparent from the description and the appended figures.

It should be noted that the previously mentioned features and the features to be further described in the following are usable not only in the respectively indicated combination, but also in further combinations or taken alone, without departing from the scope of the present invention.

SHORT DESCRIPTION OF THE FIGURES

DETAILED DESCRIPTION

Figure 1:
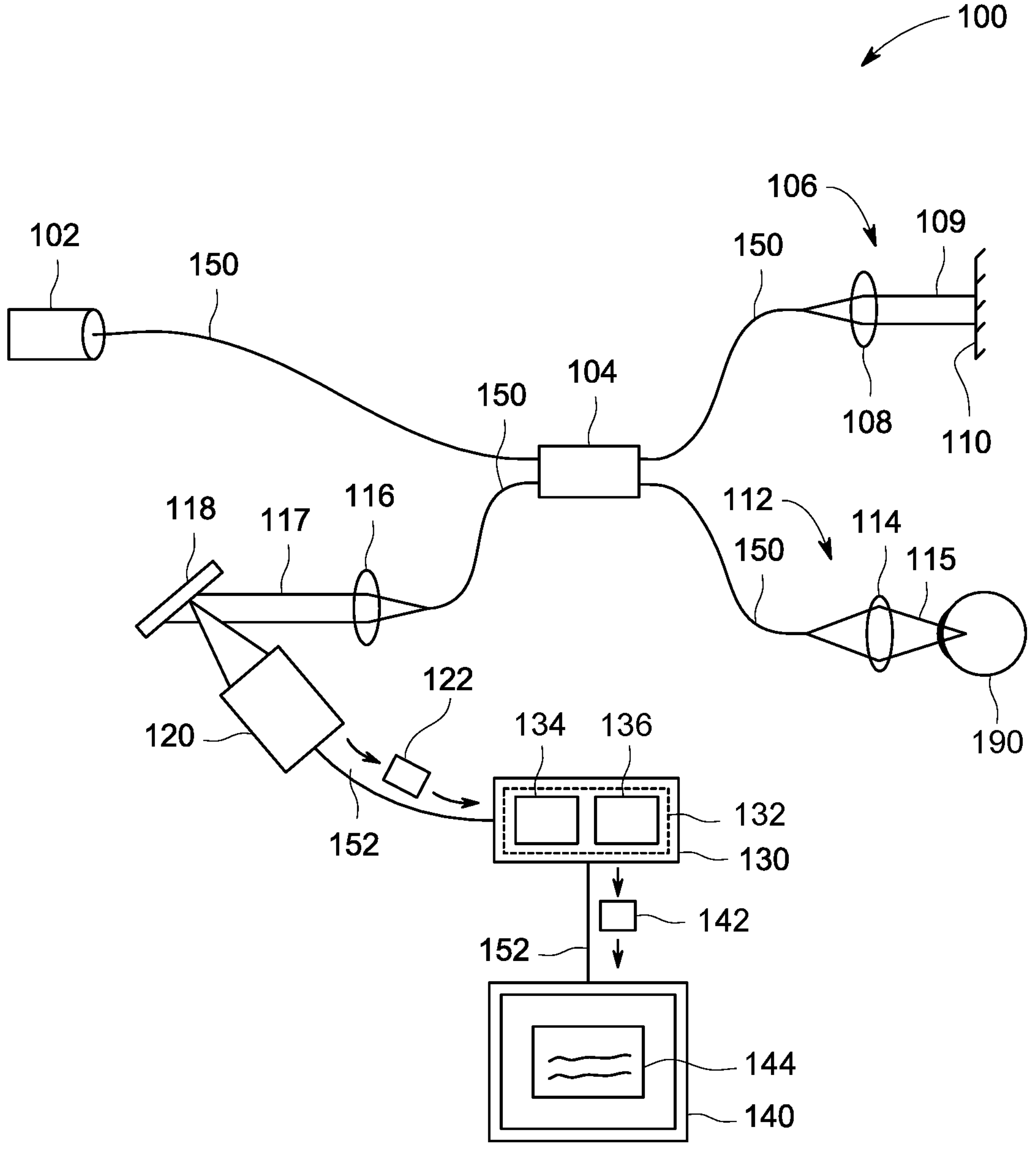
FIG. 1 shows a schematic overview of an OCT imaging system according to the invention in a preferred embodiment.

In FIG. 1, a schematic overview of an optical coherence tomography (OCT) imaging system 100 according to the invention in a preferred embodiment is shown. The OCT imaging system 100 comprises a light source 102 (e.g., a low coherence light source), a beam splitter 104, a reference arm 106, a sample arm 112, a diffraction grating 118, a detector 120 (e.g., a camera), a control unit 130 and display means 140 (e.g., a display or monitor).

Light originating from the light source 102 is guided, e.g., via fiber optic cables 150, to the beam splitter 104 and a first part of the light is transmitted through the beam splitter 104 and is then guided, via optics 108 (which is only schematically shown and represented by a lens) in order to create a light beam 109 to a reference mirror 110, wherein the optics 106 and the reference mirror 110 are part of the reference arm 106.

Light reflected from the reference mirror 110 is guided back to the beam splitter 104 and is transmitted through the beam splitter 104 and is then guided, via optics 116 (which is only schematically shown and represented by a lens) in order to create a light beam 117 to the diffraction grating 118.

A second part of the light, originating from the light source 102 and transmitted through the beam splitter 104 is guided via optics 114 (which is only schematically shown and represented by a lens) in order to create a light beam 115 (for scanning) to the subject 190 to be imaged, which, by means of example, is an eye. The optics 114 are part of the sample arm 112.

Light reflected from the subject 190 or the tissue material therein is guided back to the beam splitter 104 and is transmitted through the beam splitter 104 and is then guided, via optics 116 to the diffraction grating 118. Thus, light reflected in the reference arm 106 and light reflected in the sample arm 112 are combined by means of the beam splitter 104 and are guided, e.g., via a fiber optic cable 150, and in a combined light beam 117 to the diffraction grating 118.

Light reaching the diffraction grating 118 is diffracted and captured by the detector 120. In this way, the detector 120, which acts as a spectrometer, creates or acquires scan data or scan data sets 122 that are transmitted, e.g., via an electrical cable 152, to the control unit 130. The control unit 130 comprises a processing system 132, which comprises two processing units 134 and 136, each, e.g., being a CPU or a GPU. For example, the control unit 130 can also be equivalent to the processing system 132. A scan data set 122 is then processed to obtain image data set 142 that is transmitted, e.g., via an electrical cable 152, to the display means 140 and displayed as a real-time image 144, i.e., an image that represents the currently scanned subject 190 in real-time.

The process in which the intensity scan data set 122 is processed or converted to the image data set 142 that allows displaying of the scanned subject 190 on the display means 140 will be described in more detail in the following. Note that there are two processes, the image processing process to be performed on processing unit 134 and the dispersion coefficient adapting process to be performed on processing unit 136.

Figure 2:
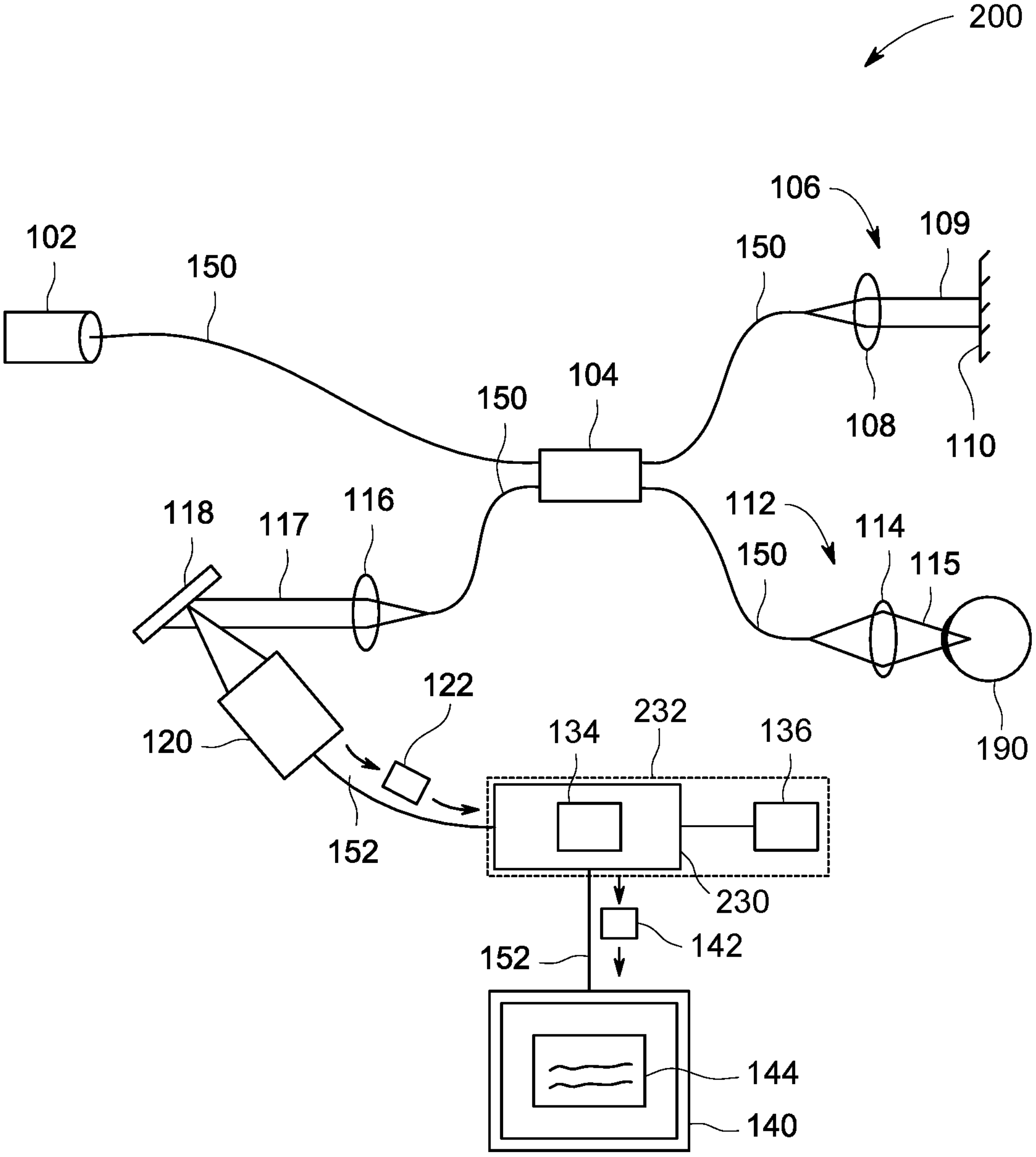
FIG. 2 shows a schematic overview of an OCT imaging system according to the invention in a further preferred embodiment.

In FIG. 2, a schematic overview of an optical coherence tomography (OCT) imaging system 200 according to the invention in a further preferred embodiment is shown. The OCT imaging system 200 basically corresponds to the OCT imaging system 100 shown in and described with respect to FIG. 1. The processing system 232, however, is different from processing system 132 of FIG. 1. Control unit 130 is comprised in the processing system 232 and it comprises processing unit 134. In particular, processing unit 134 may be equivalent with control unit 130. Processing unit 136, however, is provided separately from processing unit 134 and is connected via a connection like an ethernet connection or over internet.

The process in which the intensity scan data set 122 is processed or converted to the image data set 142 that allows displaying of the scanned subject 190 on the display means 140 is or may be equivalent as for the OCT imaging system 100 of FIG. 1 and will be described in more detail in the following. Note that also in this embodiment, the image processing process is to be performed on processing unit 134 and the dispersion coefficient adapting process is to be performed on processing unit 136.

Figure 3:
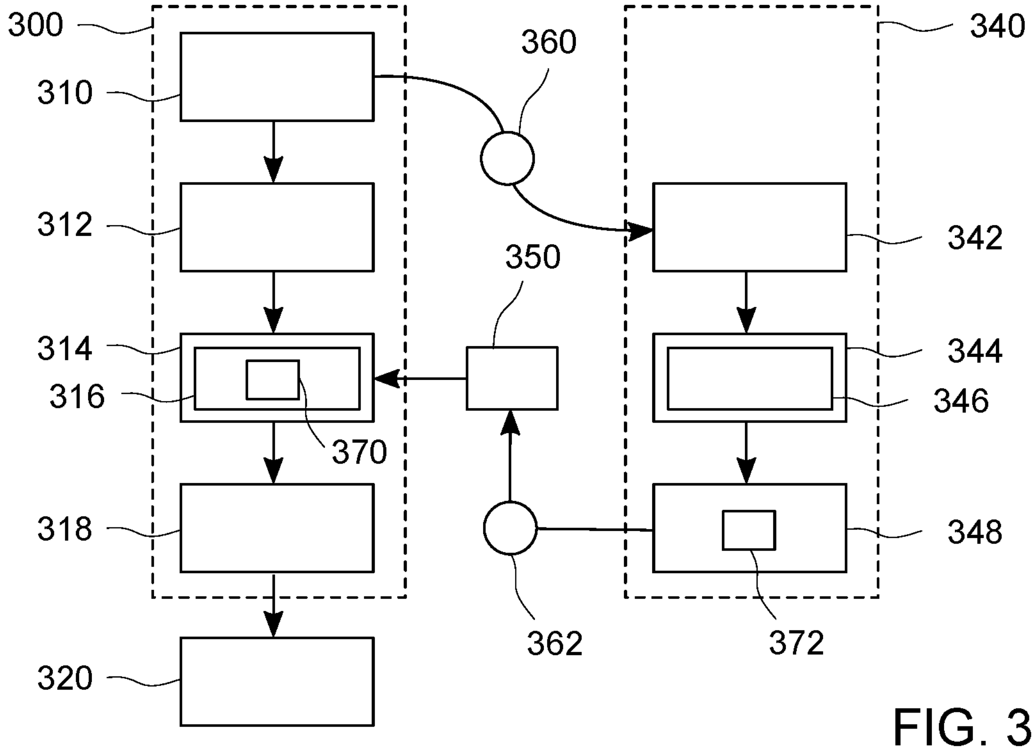
FIG. 3 shows, schematically, a flow scheme describing a method according to the invention in a preferred embodiment.

In FIG. 3, a flow scheme describing a method according to the invention in a preferred embodiment is shown schematically. For providing a real-time OCT image, an image processing process 300 is repeatedly performed, within which scan data is acquired and image data is provided to be displayed as an image or OCT image on display means as described with respect to FIG. 1 and FIG. 2. This image processing process 300 is to be repeatedly performed on or using processing unit 134 (see FIGS. 1 and 2).

The image processing process 300 starts with a step 310 of acquiring a scan data set from the subject by means of optical coherence tomography. The scan data set (see reference numeral 122 in FIGS. 1 and 2) includes one or serval spectra, each corresponding to an A-scan of the subject. In a step 312, the scan data set including is received at the processing system, in particular, at the corresponding (first) processing unit 134. Note that (depending on the definition) step 310 of acquiring the scan data set may also be considered as not being part of the image processing process; but it may considered being performed prior to actual image processing. This, however, is not essential to the invention.

In a step 314, data processing is performed on the scan data set or spectra included therein, respectively. Typically, such data processing includes DC or baseline removal, spectral filtering, wavenumber resampling, dispersion correction, Fourier transform, scaling, image filtering, and optionally additional image enhancement steps. In particular, applying the dispersion correction, step 316, is important with respect to the present invention. This dispersion correction is based on a current set 370 of dispersion coefficients, i.e. a set of dispersion coefficients that are currently present in the image processing process to be used for dispersion correction. The process of whether or not to update such dispersion coefficients will be described later. In this step, a phase correction for the spectra is computed in order to compensate for the dispersion and applied. For example, a dispersed cross-spectral density function (intensity as a function of wavelength or frequency, basically corresponding to a spectrum) can be multiplied with a phase term.

The dispersion coefficients are, for example, used in a second and third order polynomial that adds a certain amount of phase across each wavelength acquired in the OCT spectral data. This phase will either sharpen or blur the image depending on how closely it matches the effects of dispersion in the sample. For further information on how to basically apply such dispersion correction on a spectrum or scan data based on dispersion coefficients, it is also referred to the documents mentioned above.

After having applied the dispersion correction, in step 318, a dispersion corrected image data set (see reference numeral 142 in FIGS. 1 and 2) is provided; this image data set will be used in step 320 to display the corresponding OCT image on display means as described with respect to FIGS. 1 and 2.

The dispersion coefficient adapting process 340 is to be repeatedly performed on or using processing unit 136 (see FIGS. 1 and 2). As mentioned before, this process is performed simultaneously with the image processing process 300. In the dispersion coefficient adapting process 340, the latest scan data set available and being acquired in step 310, is received in step 342. A check 360 can be performed, whether a buffer used for the dispersion coefficient adapting process 340 is free, i.e., whether the dispersion coefficient adapting process can start with a new cycle (after having finished the prior one).

Then, in step 344, the dispersion coefficients are adapted by means of an optimization process 346 performed on the received scan data set. As a result, a set 372 of adapted dispersion coefficients is obtained. A more detailed explanation of step 344 will be provided later with respect to FIG. 4. Next, the set 372 of adapted dispersion coefficient is provided in step 348, these adapted coefficients to be used to update the current set 370 of dispersion coefficients.

In step 350, the current set 370 of dispersion coefficients is updated based on the set 372 of adapted dispersion coefficients. Preferably, a check 362 whether one or more criteria are met, in order to determine on whether the current set of dispersion coefficients shall be updated or not is performed prior to updating. A more detailed explanation of that check and criteria will be provided later with respect to FIG. 5.

Figure 4:
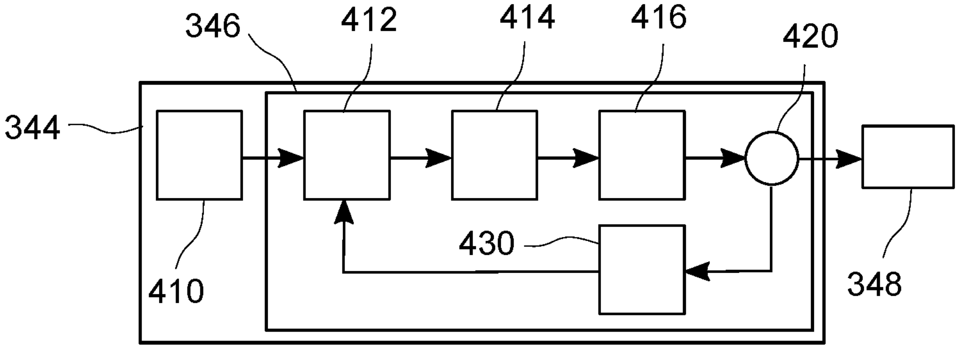
FIG. 4 shows, schematically, a flow scheme describing part of a method according to the invention in a preferred embodiment.

In FIG. 4, a flow scheme describing part of a method according to the invention in a preferred embodiment is shown, in particular, describing step 344 of adapting the dispersion coefficients, including an optimization process 346. After having received the latest available scan data set in step 342 (see FIG. 3), spectral pre-processing is performed on that data in step 410. Such pre-processing may include baseline or DC removal from the (raw) spectrum (typically made for each of serval spectra or A-scans), filtering and resampling.

Then, in step 412 a set of dispersion coefficients is used to compute and apply phase correction on the scan data set. The set of dispersion coefficients used in this step can be the set that was provided in the prior cycle in step 348 to the image processing process (see FIG. 3). Then, in step 414, a Fourier transform of the data with phase correction having been applied is performed, resulting in an OCT image. Note that this may comprise combining transformed data of several A-scans. In step 416, an image quality metric is applied to that OCT image. This may be based on a maximum image intensity, a sharpness of the image, brightness of the image, and an overall signal-to-noise ration of the image or another metric to check whether the OCT image is of high quality with respect to e.g., sharpness.

In step 420, a check on whether the metric or its result is stable or is improving with respect to e.g., a prior result of the metric. If the metric is stable, the set of dispersion coefficients used for the correction on which the OCT image is based on can be considered sufficiently good for further use. Thus, this set of dispersion coefficients can be provided in step 348 as the set 372 of adapted dispersion coefficients mentioned with respect to FIG. 3.

If in step 420, however, the metric is not stable or is improving, the set of dispersion coefficients used for the correction on which the OCT image is based on, are considered not sufficiently good for further use but are improved or further optimized in step 430. This may include, for example, a gradient decent or Nelder-Mead process. Such improved (or amended) set of dispersion coefficient are then again used in step 412 and the following ones. The process described—it is the optimization process 346—is performed until the metric is stable when checked in step 420. Afterwards, a new cycle of the dispersion coefficient adapting process 340 can be started, using the then latest available scan data set.

From the explanation of this optimization process 346—it is an iterative process—it is also clear, that the duration of it may differ from cycle to cycle, depending on how long or how many iterations it takes until the metric is stable. Note that it may also be the case that the set of adapted dispersion coefficients does not differ from the current set 370. Then, updating is not necessary.

Figure 5:
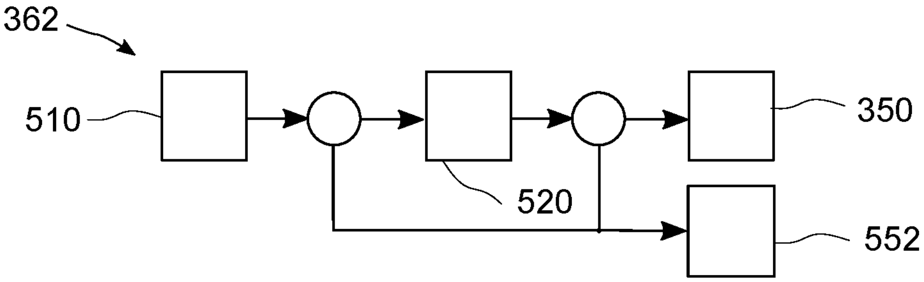
FIG. 5 shows schematically, a flow scheme describing a further part of a method according to the invention in a preferred embodiment.

In FIG. 5, a flow scheme describing a further part of a method according to the invention in a preferred embodiment is shown, in particular, describing the check 362 whether criteria are met in order to decide on whether or not to update the coefficients.

A first criterion 510 that can be checked as to whether it is met requires that a magnitude of a change of the dispersion coefficients with respect to the dispersion coefficients of the current set is above a threshold. This can apply, for example, in cumulative manner for each coefficient of the set (if several coefficients are included in a set) or for each coefficient in the set. For example, the criterion 510 can be considered met, if at least one of the coefficients has changed in its magnitude by at least 5% (or any other suitable value, e.g., 2%, 3%, 10%, 15% or 20%). If criterion 510 is not met, the updating 350 (see FIG. 3) is not performed, as expressed with step 552. Thus, minor or not necessary updates or changes are avoided.

If criterion 510 is met, a further criterion 520 can be required to be met. This further criterion can require a check that the OCT image on which the optimization was performed was an upright (or real) image and not on the inverted image (which is also obtained within OCT). If criterion 520 is not met, the updating 350 (see FIG. 3) is not performed, as expressed with step 552. Thus, incorrect dispersion correction is avoided. If, however, also criterion 520 is met, updating 350 can or will be performed.

It is to be noted that such check 362 can also be omitted and updating is performed after each cycle of the dispersion coefficient adapting process. Also, only one of the criteria mentioned with respect to FIG. 5 could be used.

With such continually and simultaneously performed adaption (or improvement) of dispersion coefficients, cases where the sample (subject) dynamically changes its dispersion properties during live or real-time imaging can be imaged in OCT with sufficiently good quality. For example, dynamic dispersion can occur during surgical procedures when air or fluids are introduced into the sample (e.g., a human eye), thus changing the dispersion properties of the optical media in the sample arm. Typically, if dispersion changes in the sample, the optimization process must be manually executed to re-compute new optimized coefficients, potentially requiring imaging to stop until the optimization is completed. This problem is overcome with the proposed technique.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Some embodiments relate to an OCT imaging system comprising a processing system as described in connection with one or more of the FIGS. 1 to 4. Alternatively, a OCT imaging system may be part of or connected to a processing system as described in connection with one or more of the FIGS. 1 to 4. FIG. 1 shows a schematic illustration of a OCT imaging system 100 configured to perform a method described herein. The OCT imaging system 100 comprises OCT imaging means and a processing or computer system 132. The OCT imaging means are configured to take images and are connected to the processing system 130. The processing system 132 is configured to execute at least a part of a method described herein. The processing system 132 may be configured to execute a machine learning algorithm. The processing system 132 and OCT imaging system 100 may be separate entities but can also be integrated together in one common housing. The processing system 130 may be part of a central processing system of the OCT imaging system and/or the processing system 132 may be part of a subcomponent of the OCT imaging system 100, such as a sensor, an actor, a camera or an illumination unit, etc. of the OCT imaging system 100.

The processing system 132 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The processing system 130 may comprise any circuit or combination of circuits. In one embodiment, the processing system 130 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the processing system 132 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The processing system 130 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The processing system 130 may also include a display device, one or more speakers, and a keyboard and/or controller, which can include a mouse, trackball, touch screen, voice-recognition device, or any other device that permits a system user to input information into and receive information from the processing system 132.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS

100, 200 OCT imaging system
102 light source
104 beam splitter
106 reference arm
108, 114, 116 optics
109, 115, 117 light beams
110 reference mirror
112 sample arm
118 diffraction grating
120 detector
122 intensity scan data
130 control unit
132, 232 processing system
134, 136 processing units
140 display means
142 image data set
150 fiber optic cable
152 electrical cable
190 subject
300 image processing process
310-320 method steps
340 dispersion coefficient adapting process
342-350 method steps
360, 362 checking steps
370 current set of dispersion coefficients
372 set of adapted dispersion coefficients
410-430, 552 method steps
510, 520 criteria

The invention claimed is:

1. A processing system for use with optical coherence tomography for imaging a subject, wherein the processing system is configured to repeatedly perform an image processing process, and independently from and in parallel to the image processing process, repeatedly perform a dispersion coefficient adapting process, wherein the image processing process comprises:

receiving a scan data set from the subject being acquired by optical coherence tomography, performing data processing on the scan data set, including applying dispersion correction based on a current set of dispersion coefficients, and providing a dispersion corrected image data set of the subject for an image of the subject to be displayed;

wherein the dispersion coefficient adapting process comprises:

receiving a latest scan data set available from the subject acquired by optical coherence tomography, adapting the dispersion coefficients by an optimization process performed on the latest scan data set, and providing a set of adapted dispersion coefficients to be used to update the current set of dispersion coefficients; and wherein the processing system is further configured to update the current set of dispersion coefficients based on the set of adapted dispersion coefficients upon the set of adapted dispersion coefficients being available from performance of the dispersion coefficient adapting process.

2. The processing system of claim 1, comprising two processing units configured to be run in parallel, a first one of the processing units being configured to perform the image processing process, and a second one of the processing units being configured to perform the dispersion coefficient adapting process.

3. The processing system of claim 1, being configured to repeatedly perform the image processing process in order to provide real-time imaging of the subject, wherein a new scan data set is used in each cycle of the image processing process.

4. The processing system of claim 1, being configured to update the current set of dispersion coefficients based on the set of adapted dispersion coefficients after each cycle of the dispersion coefficient adapting process.

5. The processing system of claim 1, being configured to update the current set of dispersion coefficients based on the set of adapted dispersion coefficients upon determining that at least one updating criterion is met.

6. The processing system of claim 5, wherein the at least one updating criterion comprises a magnitude of a change of at least one of the dispersion coefficients between a current value and an adapted value being above a threshold.

7. The processing system of claim 1, wherein the optimization process is performed on an image based on the latest scan data set and uses an image quality metric based on at least one of a maximum image intensity, a sharpness of the image, a brightness of the image, or an overall signal-to-noise ratio of the image.

8. The processing system of claim 1, wherein the scan data set from the subject is acquired by spectral domain optical coherence tomography.

9. An optical coherence tomography imaging system for imaging a subject, comprising the processing system of claim 1 and optical coherence tomography imaging means.

10. The optical coherence tomography imaging system of claim 9, comprising a control unit configured to control the optical coherence tomography imaging means, the control unit comprising a first processing unit being configured to perform the image processing process, and a second processing unit being configured to perform the dispersion coefficient adapting process.

11. The optical coherence tomography imaging system of claim 9, comprising a control unit configured to control the optical coherence tomography imaging means, the control unit comprising a first processing unit being configured to perform the image processing process, and the optical coherence tomography imaging system comprising a second processing unit being configured to perform the dispersion coefficient adapting process, the second processing unit being provided separately from the control unit.

12. The optical coherence tomography imaging system of claim 9, wherein the optical coherence tomography imaging system is used during a surgical procedure being performed on the subject.

13. A method for imaging a subject using optical coherence tomography, the method comprising:

repeatedly performing an imaging processing process by:

acquiring a scan data set from the subject by optical coherence tomography, performing data processing on the scan data set, including applying dispersion correction on the scan data set based on a current set of dispersion coefficients, and providing a dispersion corrected image data set of the subject for an image of the subject;

independently from and in parallel to the image processing process, repeatedly performing a dispersion coefficient adapting process by:

receiving a latest scan data set available from the subject acquired by optical coherence tomography, adapting the dispersion coefficients by an optimization process performed on the latest scan data set, and providing a set of adapted dispersion coefficients; and updating the current set of dispersion coefficients based on the set of adapted dispersion coefficients upon the set of adapted dispersion coefficients being available from performance of the dispersion coefficient adapting process.

14. The method of claim 13, wherein the dispersion coefficient adapting process and the imaging processing process are run on different processing units.

15. A non-transitory, computer-readable medium comprising a program code that when the program code is executed on a processor, a computer, or a programmable hardware component, causes the processor, the computer, or the programmable hardware component to perform the method of claim 13.

* * * * *